United States Patent [19]

Labrie

[11] Patent Number: 5,753,639
[45] Date of Patent: May 19, 1998

[54] LOW DOSE ANDROGENIC COMPOUNDS FOR PREVENTION AND TREATMENT OF ENDOMETRIOSIS

[75] Inventor: Fernand Labrie, Ste-Foy, Canada

[73] Assignee: Endorecherche Inc., Quebec, Canada

[21] Appl. No.: 582,629

[22] Filed: Jan. 4, 1996

Related U.S. Application Data

[60] Continuation of Ser. No. 481,620, Jun. 7, 1995, abandoned, which is a division of Ser. No. 282,964, Jul. 29, 1994, Pat. No. 5,545,634, which is a division of Ser. No. 15,083, Feb. 8, 1993, Pat. No. 5,362,720, which is a continuation of Ser. No. 724,532, Jun. 28, 1991, abandoned.

[51] Int. Cl.$^6$ .................................................. A61K 31/56
[52] U.S. Cl. .................. 514/169; 514/170; 514/177; 514/179; 514/964; 514/965; 523/113; 424/422
[58] Field of Search .................................... 514/169, 170, 514/177, 179, 964, 965; 523/113; 424/422

[56] References Cited

U.S. PATENT DOCUMENTS

| | | | |
|---|---|---|---|
| 3,773,919 | 11/1973 | Boswell | 424/19 |
| 4,522,831 | 6/1985 | Chatterton, Jr. | 424/19 |
| 4,736,849 | 4/1988 | Leonard et al. | 206/534 |
| 4,789,726 | 12/1988 | Hutchinson | 528/354 |
| 4,826,831 | 5/1989 | Plunkett et al. | 514/169 |
| 4,863,744 | 9/1989 | Urquhart et al. | 424/484 |
| 5,023,080 | 6/1991 | Gupta et al. | 424/405 |
| 5,043,331 | 8/1991 | Hirvonen et al. | 514/170 |
| 5,362,720 | 11/1994 | Labrie | 514/169 |
| 5,434,146 | 7/1995 | Labrie | 514/169 |

FOREIGN PATENT DOCUMENTS

| | | |
|---|---|---|
| 0058481 | 8/1982 | European Pat. Off. . |
| 4036425 | 5/1991 | Germany . |
| 141652 | 6/1967 | New Zealand . |
| 145613 | 7/1969 | New Zealand . |
| 180683 | 4/1976 | New Zealand . |
| 180684 | 4/1976 | New Zealand . |
| 222761 | 12/1987 | New Zealand . |
| 2239798 | 7/1991 | United Kingdom . |
| 9010462 | 9/1980 | WIPO . |
| 8903678 | 5/1989 | WIPO . |

OTHER PUBLICATIONS

Merck Index p. 909 nr. 5677, 910, nr. 5687 (1989).
Merck Index p. 1194 nr. 7486 (11th Ed.) (1989).
Anderson, et al., *Contraception* 13(3):375–384 (1976).
Said, et al., *Contraception* 37(1):1–20 (1988).
Poulin, et al., *Breast Cancer Research and Treatment* 12:213–325 (1988).
Poulin, et al., *Breast Cancer Research and Treatment* 13:161–172 (1989).
Chem. Abstr. 97(4) 28542e (1982).

*Primary Examiner*—Nathan M. Nutter
*Attorney, Agent, or Firm*—Ostrolenk, Faber, Gerb & Soffen, LLP

[57] ABSTRACT

A method of treatment or prevention of breast and endometrial cancer, osteoporosis and endometriosis in susceptible warm-blooded animals comprising administering a low dose of a progestin or other steroid derivative having androgenic activity and low masculinizing activity. Pharmaceutical compositions useful for such treatment and pharmaceutical kits containing such compositions are disclosed. An in vitro assay permitting specific measurements of androgenic activity of potentially useful compounds is also disclosed.

18 Claims, 2 Drawing Sheets

LOW DOSE ANDROGENIC COMPOUNDS FOR PREVENTION AND TREATMENT OF ENDOMETRIOSIS

This is a continuation of application Ser. No. 08/481,620, filed Jun. 7, 1995, and now abandoned which in turn is a divisional of application Ser. No. 08/282,964, filed Jul. 29, 1994 and now U.S. Pat. No. 5,545,634, which is in turn a divisional of application Ser. No. 08/015,083, filed Feb. 8, 1993 and now U.S. Pat. No. 5,362,720, which is in turn a continuation of application Ser. No. 07/724,532, filed Jun. 28, 1991 and now abandoned.

BACKGROUND OF THE INVENTION

This invention relates to a method for treating or preventing breast and endometrial cancer, bone loss, and for treating endometriosis in susceptible warm-blooded animals including humans involving administration of a compound possessing androgenic activity, and to kits containing active ingredients to be used in the therapy.

Various investigators have been studying hormonal therapy for breast and endometrial cancer as well as for the prevention and treatment of bone loss and for treatment of endometriosis. The main approaches for the treatment of already developed breast cancer are related to the inhibition of estrogen action and/or formation. The role of estrogens in promoting the growth of estrogen-sensitive breast cancer is well recognized (Lippman, Semin. Oncol. 10 (suppl. 4): 11–19, 1983; Sledge and McGuire, Cancer Res. 38: 61–75, 1984; Wittliff, Cancer 53: 630–643, 1984; Poulin and Labrie, Cancer Res. 46: 4933–4937, 1986).

Estrogens are also known to promote the proliferation of normal endometrium. Chronic exposure to estrogens unopposed by progesterone can lead to the development of endometrial hyperplasia which predisposes to endometrial carcinoma (Lucas, Obstet. Gynecol. Surv. 29: 507–528, 1974). The incidence of endometrial cancer increases after menopause, especially in women receiving estrogen therapy without simultaneous treatment with progestins (Smith et al., N. Engl. J. Med. 293: 1164–1167, 1975; Mack et al., N. Engl. J. Med. 294: 1262–1267,1976).

Various investigators have been studying hormone-dependent breast and endometrial cancer. A known form of endocrine therapy in premenopausal women is castration most commonly performed by surgery or irradiation, two procedures giving irreversible castration. Recently, a reversible form of castration has been achieved by utilizing Luteinizing Hormone-Releasing Hormone Agonists (LHRH agonists) which, following inhibition of secretion of bioactive Luteinizing Hormone (LH) by the pituitary gland, decrease serum estrogens to castrated levels (Nicholson et al., Brit J. Cancer 39: 268–273, 1979).

Several studies show that treatment of premenopausal breast cancer patients with LHRH agonists induces responses comparable to those achieved with other forms of castration (Klijn et al., J. Steroid Biochem. 20: 1381, 1984; Manni et al., Endocr. Rev. 7: 89=94, 1986). Beneficial effects of treatment with LHRH agonists have also been observed in postmenopausal women (Nicholson et al., J. Steroid Biochem. 23: 843–848, 1985).

U.S. Pat. No. 4,071,622 relates to the use of certain LHRH agonists against DMBA-induced mammary carcinoma in rats.

U.S. Pat. No. 4,775,660 relates to the treatment of female breast cancer by use of a combination therapy comprising administering an antiandrogen and an antiestrogen to a female after the hormone output of her ovaries has been blocked by chemical or surgical means.

U.S. Pat. No. 4,775,661 relates to the treatment of female breast cancer by use of a therapy comprising administering to a female, after the hormone output of her ovaries has been blocked by chemical or surgical means, an antiandrogen and optionally certain inhibitors of sex steroid biosynthesis.

U.S. Pat. No. 4,760,053 describes a treatment of selected sex steroid dependent cancers which includes various specified combinations of compounds selected from LHRH agonists, antiandrogens, antiestrogens and certain inhibitors of sex steroid biosynthesis.

In U.S. Pat. No. 4,472,382 relates to treatment of prostatic adenocarcinoma, benign prostatic hypertrophy and hormone-dependent mammary tumors with specified pharmaceuticals or combinations. Various LHRH agonists and antiandrogens are discussed.

International Patent Application PCT/W086/01105, discloses a method of treating sex steroid dependent cancers in warm-blooded animals which comprises administering specific pharmaceuticals and combinations. Antiandrogens, antiestrogens, certain inhibitors of sex steroid biosynthesis and blocking of hormonal output are discussed.

The inventor's co-pending U.S. patent application Ser. No 07/321926 filed Mar. 10, 1989, relates to a method of treatment of breast and endometrial cancer in susceptible warm-blooded animals which may include inhibition of ovarian hormonal secretion by surgical means (ovariectomy) or chemical means (use of an LHRH agonist, e.g. [D-Trp$^6$, des-Gly-NH$_2$$^{10}$]LHRH ethylamide, or antagonists) as part of a combination therapy. Antiestrogens, androgens, progestins, inhibitors of sex steroid formation (especially of 17β-hydroxysteroid dehydrogenase- or aromatase-catalyzed production of sex steroids), inhibitors of prolactin secretion and of growth hormone secretion and ACTH secretion are discussed.

Androgen receptors have been shown to be present in normal (Witliff, In: Bush, H. (Ed.), Methods in Cancer Res., Vol. 11, Acad. Press, New York, 1975, pp: 298–304; Allegra et al., Cancer Res. 39: 1447–1454, 1979) and neoplastic (Allegra et al., Cancer Res. 39: 1147–1454, 1979; Engelsman et al., Brit. J. Cancer 30: 177–181, 1975; Moss et al., J. Ster. Biochem. 6: 743–749, 1975; Miller et al., Eur. J. Cancer Clin. Oncol. 2: 539–542, 1985; Lippman et al., Cancer 38: 868–874, 1976; Allegra et al., Cancer Res. 39: 1447–1454, 1979; Miller et al., Eur. J. Clin. Oncol. 21: 539–542, 1985; Lea et al., Cancer Res. 49: 7162–7167, 1989) as well as in several established breast cancer cell lines (Lippman et al., Cancer Res. 36: 4610–4618, 1976; Horwitz et al., Cancer Res. 38: 2434–2439, 1978; Poulin et al., Breast Cancer Res. Treatm. 12: 213–225, 1988). Androgen receptors are also present in dimethylbenz(a)anthracene (DMBA)-induced mammary tumors in the rat (Asselin et al., Cancer Res. 40: 1612–1622, 1980).

Androgen receptors have also been described in human endometrium (MacLaughlin and Richardson, J. Steroid Biochem. 10: 371–377, 1979; Muechler and Kohler, Gynecol. Invest. 8: 104, 1988). The growth inhibitory effects of the androgen methyltrienolone (R1881), on endometrial carcinoma in vitro have been described (Centola, Cancer Res. 45: 6264–6267,1985).

Recent reports have indicated that androgen receptors may add to the selective power of estrogen receptors or even supplant estrogen receptors as best predicting response to endocrine therapy (Teulings et al., Cancer Res. 40: 2557–2561, 1980; Bryan et al., Cancer 54: 2436–2440, 1984).

The first androgen successfully used in the treatment of advanced breast cancer is testosterone propionate (Nathanson, Rec. Prog. Horm. Res. 1: 261–291, 1947). Many studies subsequently confirmed the beneficial effect of androgens on breast cancer (Alan and Herrman, Ann. Surg. 123: 1023–1035; Adair, Surg. Gynecol. Obstet. 84: 719–722, 1947; Adair et al., JAMA 140: 1193–2000, 1949). These initial results stimulated cooperative studies on the effect of testosterone propionate and DES which were both found to be effective in producing objective remissions. (Subcommittee on Steroid and Cancer of the Committee on Research of the Council on Pharmacy and Chemistry of the Am. Med. Association followed by the Cooperative Breast Cancer Group under the Cancer Chemotherapy National Service Center of the NCI who found that testosterone propionate improved remission rate and duration, quality of life and survival (Cooperative Breast Cancer Group, JAMA 188, 1069–1072, 1964)).

A response rate of 48% (13 of 27 patients) was observed in postmenopausal women who received the long-acting androgen methonolone enanthate (Kennedy et al., Cancer 21: 197–201, 1967). The median duration of survival was four times longer in the responders as compared to the non-responder group (27 versus 7.5 months). A large number of studies have demonstrated that androgens induce remission in 20 to 40% of women with metastatic breast cancer (Kennedy, Hormone Therapy in Cancer. Geriatrics 25: 106–112, 1970; Goldenberg et al., JAMA 223: 1267–1268, 1973).

A response rate of 39% with an average duration of 11 months has recently been observed in a group of 33 postmenopausal women who previously failed or did not respond to Tamoxifen (Manni et al., Cancer 48: 2507–2509, 1981) upon treatment with Fluoxymesterone (Halostatin) (10 mg, b.i.d.). Of these women, 17 had also undergone hypophysectomy. There was no difference in the response rate to Fluoxymesterone in patients who had previously responded to Tamoxifen and in those who had failed. Of the 17 patients who had failed to both Tamoxifen and hypophysectomy, 7 responded to Fluoxymesterone for an average duration of 10 months. Among these, two had not responded to either Tamoxifen or hypophysectomy.

The combination Fluoxymesterone and Tamoxifen has been shown to be superior to Tamoxifen alone. In fact, complete responses (CR) were seen only in the combination arm while 32% showed partial response (PR) in the combination arm versus only 15% in the monotherapy arm. In addition, there were only 25% of non-responders in the combination therapy arm versus 50% in the patients who received TAM alone (Tormey et al., Ann. Int. Med. 98: 139–144, 1983). Moreover, the median time from onset of therapy to treatment failure was longer with Fluoxymesterone+Tamoxifen (180 days) compared to the Tamoxifen arm alone (64 days). There was a tendency for improved survival in the combination therapy arm (380 versus 330 days).

The independent beneficial effect of an androgen combined with an antiestrogen is suggested by the report that patients who did not respond to Tamoxifen could respond to Fluoxymesterone and vice versa. Moreover, patients treated with Tamoxifen and crossing over to Fluoxymesterone survived longer that those treated with the reverse regimen (Tormey et al., Ann. Int. Med. 98: 139–144, 1983).

Since testosterone propionate had beneficial effects in both pre- and postmenopausal women (Adair et al., J. Am. Med. Ass. 15: 1193–1200, 1949), it indicates that in addition to inhibiting gonadotropin secretion, the androgen exerts a direct inhibitory effect on cancer growth.

Recent in vitro studies describe the relative antiproliferative activities of an androgen on the growth of the estrogen-sensitive human mammary carcinoma cell line ZR-75-1 (Poulin et al. "Androgens inhibit basal and estrogen-induced cell proliferation in the ZR-75-1 human breast cancer cell line", Breast Cancer Res. Treatm. 12: 213–225, 1989). As mentioned above, Poulin et al. (Breast Cancer Res. Treatm. 12: 213–225, 1989) have found that the growth of ZR-75-1 human breast carcinoma cells is inhibited by androgens, the inhibitory effect of androgens being additive to that of an antiestrogen. The inhibitory effect of androgens on the growth of human breast carcinoma cells ZR-75-1 has also been observed in vivo in nude mice (Dauvois and Labrie, Cancer Res. 51: 3131–3151, 1991).

As a possible mechanism of androgen action in breast cancer, it has recently been shown that androgens strongly suppress estrogen (ER) and progesterone (PgR) receptor contents in ZR-75-1 human breast cancer cells as measured by radioligand binding and anti-ER monoclonal antibodies. Similar inhibitory effects were observed on the levels of ER mRNA measured by ribonuclease protection assay. The androgenic effect is measured at subnanomolar concentrations of the non-aromatizable androgen 5α-dihydrotestosterone, regardless of the presence of estrogens, and is competitively reversed by the antiandrogen hydroxyflutamide (Poulin et al., Endocrinology 125: 392–399, 1989). Such data on estrogen receptor expression provide an explanation for at least part of the antiestrogenic effects of androgens on breast cancer cell growth and moreover suggest that the specific inhibitory effects of androgen therapy could be additive to the standard treatment limited to blockade of estrogens by antiestrogens.

Dauvois et al. (Breast Cancer Res. Treatm. 14: 299–306, 1989) have shown that constant release of the androgen 5α-dihydrotestosterone (DHT) in ovariectomized rats bearing DMBA-induced mammary carcinoma caused a marked inhibition of tumor growth induced by 17β-estradiol ($E_2$). That DHT acts through interaction with the androgen receptor is supported by the finding that simultaneous treatment with the antiandrogen Flutamide completely prevented DHT action. Particularly illustrative of the potent inhibitory effect of the androgen DHT on tumor growth are the decrease by DHT of the number of progressing tumors from 69.2% to 29.2% in $E_2$-treated animals and the increase by the androgen of the number of complete responses (disappearance of palpable tumors) from 11.5% to 33.3% in the same groups of animals. The number of new tumors appearing during the 28-day observation period in $E_2$-treated animals decreased from 1.5±0.3 to 0.7±0.2 per rat during treatment with the androgen DHT, an effect which was also reversed by the antiandrogen Flutamide. Such data demonstrate, for the first time, that androgens are potent inhibitors of DMBA-induced mammary carcinoma growth by an action independent from inhibition of gonadotropin secretion and suggest an action exerted directly at the tumor level, thus further supporting the in vitro data obtained with human ZR-75-1 breast cancer cells (Poulin et al., Breast Cancer Res. Treatm. 12: 213–225, 1988).

The natural androgens testosterone (TESTO) and dihydrotestosterone (DHT) are formed from conversion of androstenedione into TESTO by 17β-hydroxysteroid dehydrogenase and then TESTO into DHT by the action of the enzyme 5α-reductase. The adrenal precursor 5-androst-5-ene-3β,17β-diol can also be converted into TESTO by action of the enzyme 3β-hydroxysteroid dehydrogenase/ $\Delta^5\Delta^4$ isomerase (3β-HSD).

Since the natural androgens TESTO and DHT have strong masculinizing effects, numerous derivatives of TESTO as well as progesterone have been synthesized in order to obtain useful compounds having fewer undesirable masculinizing side effects (body hair growth, loss of scalp hair, acne, seborrhea and loud voice).

Medroxyprogesterone acetate (MPA) is one of the most widely used compounds in the endocrine therapy of advanced breast cancer in women (Mattsson, Breast Cancer Res. Treatm. 3: 231-235, 1983; Blumenschein, Semin. Oncol. 10: 7-10, 1983; Hortobagyi et al., Breast Cancer Res. Treatm. 5: 321-326, 1985; Haller and Glick, Semin. Oncol. 13: 2-8, 1986; Horwitz, J. Steroid Biochem. 27: 447-457, 1987). The overall clinical response rate of high doses of this synthetic progestin averages 40% in unselected breast cancer patients (Horwitz, J. Steroid Biochem. 27: 447-457, 1987), an efficacy comparable to that of the nonsteroidal antiestrogen tamoxifen (Lippman, Semin. Oncol. 10 (Suppl.): 11-19, 1983). Its more general use, however, is for breast cancer relapsing after other endocrine therapeutic modalities. The maximal inhibitory action of medroxyprogesterone acetate (MPA) on human breast cancer cell growth in vitro may be achieved at concentration as low as 1 nM while an approximately 1000-fold higher dose is often required for glucocorticoid action (Poulin et al., Breast Cancer Res. Treatm. 13: 161-172, 1989).

Until recently, the mechanisms underlying the antitumor activity of MPA were poorly understood and have been attributed to interaction with the progesterone receptor. This steroid, however, presents a high affinity for progesterone (PgR) as well as for androgen (AR) and glucocorticoid receptors (GR) in various animal tissues (Perez-Palacios et al., J. Steroid Biochem. 19: 1729-1735, 1983; Janne and Bardin, Pharmacol. Rev. 36: 35S-42S, 1984; Pridjian et al., J. Steroid Biochem. 26: 313-319, 1987; Ojasso et al., J. Steroid Biochem. 27: 255-269, 1987) as well as in human mammary tumors (Young et al., Am. J. Obstet. Gynecol. 137: 284-292, 1980), a property shared with other synthetic progesterone derivatives (Bullock et al., Endocrinology 103: 1768-1782, 1978; Janne and Bardin, Pharmacol. Rev. 36: 35S-42S, 1984; Ojasso et al., J. Steroid Biochem. 27: 255-269, 1987). It is known that in addition to progesterone receptors (PgR), most synthetic progestational agents bind with significant affinity to androgen (AR) as well as glucocorticoid (GR) receptors, and induce biological actions specifically determined by these individual receptor systems (Labrie et al., Fertil. Steril. 28: 1104-1112, 1977; Engel et al., Cancer Res. 38: 3352-3364, 1978; Raynaud et al., In: Mechanisms of Steroid Action (G. P. Lewis, M. Grisburg, eds), MacMiland Press, London, pp. 145-158, 1981; Rochefort and Chalbos, Mol. Cell. Endocrinol. 36: 3-10, 1984; J anne and Bardin, Pharmacol. Rev. 36: 35S-42S, 1984; Poyet and Labrie, Mol. Cell. Endocrinol. 42: 283-288, 1985; Poulin et al., Breast Cancer Res. Treatm. 13: 161-172, 1989). Accordingly, several side effects other than progestational have been noted in patients treated with MPA.

The most easily explained adverse side effects of MPA are related to its glucocorticoid-like action with Cushingoid syndrome, euphoria and subjective pain relief (Mattsson, Breast Cancer Res. Treatm. 3: 231-235, 1983; Blossey et al., Cancer 54: 1208-1215, 1984; Hortobagyi et al., Breast Cancer Res. Treatm. 5: 321-326, 1985; Van Veelen et al., Cancer Chemother. Pharmacol. 15: 167-170, 1985). Suppression of adrenal function by MPA is believed to be caused both by an inhibitory action on ACTH secretion at the pituitary level and by direct inhibition of steroidogenesis at the adrenal level (Blossey et al., Cancer 54: 1208-1215, 1984; Van Veelen et al., Cancer Chemother. Pharmacol. 15: 167-170, 1985; Van Veelen et al., Cancer Treat. Rep. 69: 977-983, 1985).

Despite its high affinity for AR, MPA seldom causes significant virilizing symptoms (acne, hirsutism, etc.) (Haller and Glick, Semin. Oncol. 13: 2-8, 1986). Moreover, its inhibitory effect on gonadotropin secretion is clearly exerted through its direct interaction with pituitary AR in the rat (Labrie et al., Fertil. Steril. 28: 1104-1112, 1977; Perez-Palacios et al., J. Steroid Biochem. 19: 1729-1735, 1983) and human (Perez-Palacios et al., J. Steroid Biochem. 15: 125-130, 1981). In addition, MPA exhibits androgenic activity in the mouse kidney (Janne and Bardin, Pharmacol. Rev. 36: 35S-42S, 1980) and in the rat ventral prostate (Labrie, C. et al., J. Steroid Biochem. 28: 379-384, 1987; Labrie C. et al., Mol. Cell. Endocrinol. 68: 169-179, 1990).

Poulin et al. "Androgen and glucocorticoid receptor-mediated inhibition of cell proliferation by medroxyprogesterone acetate in ZR-75-1 human breast cancer cells", Breast Cancer Res. Treatm. 13: 161-172, 1989) have recently found that the inhibitory effect of medroxyprogesterone acetate (MPA) on the growth of the human ZR-75-1 breast cancer cells is mainly due to the androgenic properties of the compound. The androgenic properties of MPA have been demonstrated in other systems (Labrie C. et al., J. Steroid Biochem. 28: 379-384, 1987; Luthy et al., J. Steroid Biochem 31: 845-852, 1988; Plante et al., J. Steroid Biochem. 31: 61-64, 1988; Labrie C. et al., Mol. Cell. Endocrinol. 58: 169-179, 1990). Other synthetic progestins have also been shown to possess, in addition to their progesterone-like activity, various degrees of androgenic activity (Labrie et al., Fertil. Steril. 31: 29-34, 1979; Poyet and Labrie, The Prostate 9: 237-246, 1986; Labrie C. et al., J. Steroid Biochem. 28: 379-384, 1987; Luthy et al., J. Steroid Biochem. 31: 845-852, 1988; Plante et al., J. Steroid Biochem. 31: 61-64, 1989).

High dose MPA as first treatment of breast cancer has shown similar effects as Tamoxifen (Van Veelen et al., Cancer 58: 7-13, 1986). High dose progestins, especially medroxyprogesterone acetate and megestrol acetate have also been successfully used for the treatment of endometrial cancer (Tatman et al., Eur. J. Cancer Clin. Oncol. 25: 1619-1621, 1989; Podratz et al., Obstet. Gynecol. 66: 106-110, 1985; Ehrlich et al., Am. J. Obstet. Gynecol. 158: 797-807, 1988). High dose MPA is being used with a success similar to that of Tamoxifen for the treatment of endometrial carcinoma (Rendina et al., Europ. J. Obstet. Gynecol. Reprod. Biol. 17: 285-291, 1984).

In a randomized clinical trial, high dose MPA administered for 6 months has been shown to induce resolution of the disease in 50% of the patients and a partial resolution in 13% of subjects compared to 12% and 6%, respectively, in patients who received placebo (Telimaa et al., Gynecol. Endocrinol. 1: 13, 1987).

The androgen methyltestosterone has been shown to relieve the symptoms of endometriosis (Hamblen, South Med. J. 50: 743, 1987; Preston, Obstet. Gynecol. 2: 152, 1965). Androgenic and masculinizing side effects (sometimes irreversible) are however important with potent androgenic compounds such as testosterone.

In analogy with the androgen-induced decrease in estrogen receptors in human breast cancer ZR-75-1 cells (Poulin et al., Endocrinology 125: 392-399, 1989), oral administration of MPA to women during the follicular phase caused a decrease in the level of estrogen binding in the endometrium (Tseng and Gurpide, J. Clin. Endocrinol. Metab. 41, 402-404, 1975).

Studies in animals have shown that androgen deficiency leads to osteopenia while testoterone administration increases the overall quantity of bone (Silberberg and Silberberg, 1971; see Finkelstein et al., Ann. Int. Med. 106: 354–361, 1987). Orchiectomy in rats can cause osteoporosis detectable within 2 months (Winks and Felts, Calcif. Tissue Res. 32: 77–82, 1980; Verhas et al., California Tissue Res. 39: 74–77, 1986).

While hirsute oligomenorrheic and amenorrheic women having low circulating $E_2$ levels would be expected to have reduced bone mass, these women with high androgen (but low estrogen) levels are at reduced risk of developing osteoporosis (Dixon et al., Clinical Endocrinology 30: 271–277, 1989).

Adrenal androgen levels have been found to be reduced in osteoporosis (Nordin et al., J. Clin. Endocr. Metab. 60: 651, 1985). Moreover, elevated androgens in postmenopausal women have been shown to protect against accelerated bone loss (Deutsch et al., Int. J. Gynecol. Obstet. 25: 217–222, 1987; Aloia et al., Arch. Int. Med. 143: 1700–1704, 1983). In agreement with such a role of androgens, urinary levels of androgen metabolites are lower in postmenopausal symptomatic menopausis than in matched controls and a significant decrease in conjugated dehydroepiandrosterone (DHEA) was found in the plasma of osteoporotic patients (Hollo and Feher, Acta Med. Hung. 20: 133, 1964; Urist and Vincent, J. Clin. Orthop. 18: 199,1961; Hollo et al., Acta Med. Hung. 27: 155, 1970). It has even been suggested that postmenopausal osteoporosis results from both hypoestrogenism and hypoandrogenism (Hollo et al., Lancet 1357, 1976).

As a mechanism for the above-suggested role of both estrogens and androgens in osteoporosis, the presence of estrogen (Komm et al., Science 241: 81–84, 1988; Eriksen et al., Science 241: 84–86, 1988) as well as androgen (Colvard et al., Proc. Natl. Acad. Sci. 86: 854–857, 1989) receptors in osteoblasts could explain increased bone resorption observed after estrogen and androgen depletion.

In boys, during normal puberty, an increase in serum testosterone levels procedes an increase in alkaline phosphate activity (marker of osteoblastic activity) which itself precedes increased one density (Krabbe et al., Arch. Dis. Child. 54: 950–953, 1979; Krabbe et al., Arch. Pediat. Scand. 73: 750–755, 1984; Riis et al., California Tissue Res. 37: 213–217,1985).

While, in women, there is a rapid bone loss starting at menopause, bone loss in males can be recognized at about 65 years of age (Riggs et al., J. Clin. Invest. 67: 328–335, 1987). A significant bone loss is seen in men at about 80 years of age, with the accompanying occurrence of hip, spine and wrist fractures. Several studies indicate that osteoporosis is a clinical manifestation of androgen deficiency in men (Baran et al., Calcif. Tissue Res. 26: 103–106, 1978; Odell and Swerdloff, West. J. Med. 124: 446–475, 1976; Smith and Walker, California Tissue Res. 22 (Suppl.): 225–228, 1976).

Although less frequent than in women osteoporosis can cause significant morbidity in men (Seeman et al., Am. J. Med. 75: 977–983, 1983). In fact, androgen deficiency is a major risk for spinal compression in men (Seeman et al., Am. J. Med. 75: 977–983, 1983). Decreased radial and spinal bone density accompanies hypogonadism associated with hyperprolactinemia (Greenspan et al., Ann. Int. Med. 104: 777–782, 1986) or anaorexia nervosa (Rigotti et al., JAMA 256: 385–288, 1986). However, in these cases, the role of hyperprolactinemia and loss in body weight is uncertain.

Hypogonadism in the male is a well-recognized cause of osteoporotic fracture (Albright and Reinfenstein, 1948; Saville, Clin. End. Metab. 2: 177–185, 1973). Bone density is in fact reduced in both primary and secondary hypogonadism (Velentzas and Karras. Nouv. Presse Médicale 10: 2520, 1981).

Severe osteopenia as revealed by decreased cortical and trabecular bone density was reported in 23 hypogonadotropic hypogonadal men (Finkelstein et al., Ann. Int. Med. 106: 354–361, 1987; Foresta et al., Horm. Metab. Res. 15: 56–57, 1983). Osteopenia has also b reported in men with Klinefelter's syndrome (Foresta et al., Horm. Metab. Res. 15: 206–207, 1983; Foresta et al., Horm. Metab. Res. 15: 56–57, 1983; Smith and Walker, California Tissue Res. 22: 225–228, 1977).

Androgenic-reversible decreased sensitivity to calcitonin has been described in rats after castration (Ogata et al., Endocrinology 87: 421, 1970; Hollo et al., Lancet 1: 1205, 1971; Hollo et al., Lancet 1: 1357, 1976). In addition, serum calcitonin has been found to be reduced in hypogonadal men (Foresta et al., Horm. Metab. Res. 15: 206–207, 1983) and testosterone therapy in castrated rats increases the hypocalcemic effect of calcitonin (McDermatt and Kidd, End. Rev. 8:377–390,1987).

Albright and Ruferstein (1948) originally suggested that androgens increase the synthesis of bone matrix. Androgens have also been shown to increase osteoid synthesis and mineralization in chicken (Puche and Rosmano, California Tissue Res. 4: 39–47, 1969). Androgen therapy in hypogonadal men increases skeletal growth and maturation (Webster and Hogkins, Proc. Soc. Exp. Biol. Med. 45: 72–75, 1940). In addition, testosterone therapy in man has been shown to cause positive nitrogen, calcium and phosphate balance (Albright, F., Reifeinstein, E. C. In: The parathyroid glands and metabolic bone disease. Williams and Williams Co.: Baltimore, pp. 145–204, 1948). As studied by bone histomorphometry, testosterone therapy in hypogonadal males resulted in increases in relative osteoid volume, total osteoid surface, linear extend of bone formation and bone mineralization (Barau et al., Calcif. Tissue Res. 26: 103–106, 1978).

Treatment with testosterone has been shown to increase osteoid surfaces and beam width with unchanged or reduced oppositional rates, thus indicating and increase in total bone mineralization rate (Peacock et al., Bone 7: 261–268, 1986). There was also a decrease in plasma phosphate probably due to an effect on renal tubular reabsorption of phosphates (Selby et al., Clin. Sci. 69: 265–271, 1985).

Cortical bone density increases in hyperprolactinemic men with hypogonadism when testicular function is normalized (Greenspan et al., Ann. Int. Med. 104: 777–782, 1986; Greenspan et al., Ann. Int. Med. 110: 526–531, 1989). Testosterone therapy increases bone formation in men with primary hypogonadism (Baron et al., Calcif. Tissue Res. 26: 103–106, 1978; Francis et al., Bone 7: 261–268, 1986).

In 21 hypogonadal men with isolated GnRH deficiency, normalization of serum testosterone for more than 12 months increased bone density (Kinkelstein et al., J. Clin. Endocr. Metab. 69: 776–783, 1989). In men with already fused epiphyses, however, there was a significant increase in cortical bone density while no significant change was observed on trabecular bone density, thus supporting previous suggestions of variable sensitivity of cortical and trabecular bone to steroid therapy.

Previous studies with anabolic steroids in small numbers of patients have suggested positive effects on bone (Lafferty et al., Ann. J. Med. 36: 514–528, 1964; Riggs et al., J. Clin. Invest. 51: 2659–2663, 1972; Harrison et al., Metabolism 20: 1107–1118, 1971). More recently, using total body calcium measurements by neutron activation as parameter, the anabolic steroid methandrostenolone has shown positive and relatively long-term (24–26 months) effects in a double-blind study in postmenopausal osteoporosis (Chessnut et al., Metabolism 26: 267–277, 1977; Aloia et al., Metabolism 30: 1076–1079, 1981).

The anabolic steroid nandrolone decanoate reduced bone resorption in osteoporotic women (Dequeker and Geusens, Acta Endocrinol. 271 (Suppl.): 45–52, 1985) in agreement with the results observed during estrogen therapy (Dequeker and Ferin, 1976, see Dequeker and Geusens). Such data confirm experimental data in rabbits and dogs when nandrolone decanoate reduced bone resorption (Ohem et al., Curr. Med. Res. Opin. 6: 606–613, 1980). Moreover, in osteoporotic women (Dequeker and Geusens, Acta Endocrinol. (Suppl.) 271: 45–52, 1985) the anabolic steroid not only reduced bone loss but also increased bone mass. Vitamin D treatment, on the other hand, only reduced bone resorption.

Therapy of postmenopausal women with nandrolone increased cortical bone mineral content (Clin. Orthop. 225: 273–277). Androgenic side effects, however, were recorded in 50% of patients. Such data are of interest since while most therapies are limited to an arrest of bone loss, an increased in bone mass was found with the use of the anabolic steroid nandrolone. A similar stimulation of bone formation by androgens has been suggested in a hypogonadal male (Baran et al., Calcif. Tissue Res. 26: 103, 1978). The problem with regimens which inhibit bone resorption with calcium, calcitriol or hormones is that they almost certainly lead to suppression of bone formation (Need et al., Mineral. Electrolyte Metabolism 11: 35, 1985). Although, Albright and Reiferestein (1948) (See Need, Clin. Orthop. 225: 273, 1987) suggested that osteoporosis is related to decreased bone formation and will respond to testosterone therapy, the virilizing effects of androgens have made them unsuitable for the treatment of postmenopausal women. Anabolic steroids, compounds having fewer virilizing effects, were subsequently developed. Although, minimal effects have been reported by some (Wilson and Griffin, Metabolism 28: 1278, 1980) more positive results have been reported (Chessnut et al., Metabolism 32: 571–580, 1983; Chessnut et al., Metabolism 26: 267, 1988; Dequeker and Geusens, Acta Endocrinol. (Suppl. 110) 271: 452, 1985). A randomized study in postmenopausal women has been shown an increase in total bone mass during treatment with the anabolic steroid stanazolol although side effects were recorded in the majority of patients (Chessnut et al., Metabolism 32: 571–580, 1983).

As mentioned above, the doses of "progestins" (for example medroxyprogesterone acetate) used for the standard therapy of breast cancer are accompanied by undesirable important side effects (especially those related to interaction of the steroid with the glucocorticoid receptor, especially Cushingoid syndrome, euphoria) (Mattsson, Breast Cancer Res. Treatm. 3: 231–235, 1983; Blossey et al., Cancer 54: 1208–1215, 1984; Hortobagyi et al., Breast Cancer Res. Treatm. 5: 321–326, 1985; Von Veelen et al., Cancer Chemother. Pharmacol. 15: 167–170, 1985).

The term "progestin" refers to derivatives of progesterone and testosterone. Such progestins have, at times, been synthesized with the aim of developing compounds acting as analogs of progesterone on the progesterone receptors, especially for the control of fertility. With the availability of new and more precise tests, however, it became evident that such compounds, originally made to interact exclusively with the progesterone receptor, do also interact, frequently with high affinity, with the androgen receptor (Labrie et al., Fertil. Steril. 28: 1104–1112, 1977; Labrie et al., Fertil. Steril. 31: 29–34, 1979; Labrie, C. et al., J. Steroid Biochem. 28: 379–384, 1987; Labrie C. et al., Mol. Cell. Endocrinol. 68: 169–179, 1990). Sometimes, the androgenic activity of these compounds, especially at low concentrations, becomes more important than the true progestin activity. This is the case, for example, for medroxyprogesterone acetate (Poulin et al., Breast Cancer Res. Treatm. 13: 161–172, 1989).

A problem with prior-art treatments of breast and endometrial cancer with synthetic progestins is the side effects observed with such treatments. The blockade of estrogens, another common treatment for breast cancer, would have undesirable deleterious effects on bone mass in women. Similarly, blockade of estrogens, a common treatment for endometriosis, has similar undesirable deleterious effects on bone mass in women.

SUMMARY OF THE INVENTION

It is an object of the present invention to provide a method for prevention and treatment of breast cancer, endometrial cancer, osteoporosis and endometriosis, while substantially avoiding undesirable side effects.

It is another object of the invention to provide a method for prevention of cancer having more specific effectiveness in delaying tumor growth.

It is another object of the invention to provide a method for prevention of breast and endometrial cancer having significantly reduced frequency of unwanted side effects.

It is another object of the invention to provide a method for prevention of bone loss in men and women having a reduced frequency of unwanted side effects.

It is another object of the invention to provide a method for prevention of bone loss in women where estrogen formation and/or action is blocked in order to treat various estrogen-sensitive diseases, including cancer.

It is another object of the invention to provide a method for prevention of bone loss in women already exposed to low estrogens following menopause.

It is a further object of the invention to provide kits and pharmaceutical compositions for use in the methods described herein.

These and other objects are achieved by practicing the methods disclosed herein and/or by utilizing the pharmaceutical compositions and kits disclosed herein.

In one embodiment, a method is provided for activating androgen receptors in a warm blooded animal, including a human, comprising administering to said animal at least one androgenic steroid having a Ki value of less than $2 \times 10^{-8} M$ for the androgen receptor, an androgen receptor-mediated inhibitory effect on the growth of human breast cancer ZR-75-1 cells which reaches half-maximal value at a concentration below 3.0 nanomoles per liter, and no visible masculinizing activity at blood serum concentrations below 50 nM, wherein every such androgenic steroid is administered at a dosage sufficiently low to maintain a cumulative serum concentration below 50 nanomoles per liter.

The methods of said androgenic steroid described herein are particularly useful for the treatment of human breast or endometrial cancer, osteoporosis or endometriosis. It is believed that the methods are also suitable for all purposes which are enhanced by administering androgens or otherwise activating androgen receptors. Both treatment and prevention of the diseases and disorders discussed herein are contemplated within the scope of the invention. It is believed that the methods of the invention are suitable for both prophylactic and therapeutic use.

The compounds utilized have the special property of possessing potent androgenic activity at low blood concentration (e.g. less than 50 nM) while exhibiting very little glucocorticoid receptor activity at those concentrations. They are also characterized by the absence of physical masculinizing activity in females at the concentration range at which they are used. This is to be distinguished from natural androgens produced in gonadal or peripheral tissues such as testosterone and dihydrotestosterone which exhibit considerable masculinizing activity even at low blood concentrations. Synthetic progestins, e.g. progesterone derivatives are useful for this invention, as are some anabolic steroids.

The androgens of the invention on average do not cause physically detectable increase in masculinizing effects such as increased hair growth in females, acne, seborrhea or hair loss. These masculinizing effects have been quantified in the literature. See, for example, Ferriman and Gallwey, J. P. Clin. Endocrinol. Metab. 21: 1440–1447, 1961 (regarding hair growth); Cremoncini et al., Acta. Eur. Fertil. 7: 248–314, 1976 (acne, seborrhea and hair loss). See also Cusan et al., J. Am. Acad. Dermatol. 23: 462–469, 1990. Tables 1 and 2 below set forth a quantification.

TABLE 1

Definition of hair grading at each of 11 sites
(Grade 0 at all sites indicates absence of terminal hair)

| Site | Grade | Definition |
|---|---|---|
| 1. Upper lip | 1 | A few hairs at outer margin |
| | 2 | A small moustache at outer margin |
| | 3 | A moustache extending halfway from outer margin |
| | 4 | A moustache extending to mid-line |
| 2. Chin | 1 | A few scattered hairs |
| | 2 | Scattered hairs with small concentrations |
| | 3 & 4 | Complete cover, light and heavy |
| 3. Chest | 1 | Circumareolar hairs |
| | 2 | With mid-line hair in addition |
| | 3 | Fusion of these areas, with three-quarter cover |
| | 4 | Complete cover |
| 4. Upper back | 1 | A few scattered hairs |
| | 2 | Rather more, still scattered |
| | 3 & 4 | Complete cover, light and heavy |
| 5. Lower back | 1 | A sacral tuft of hair |
| | 2 | With some lateral extension |
| | 3 | Three-quarter cover |
| | 4 | Complete cover |
| 6. Upper abdomen | 1 | A few mid-line hairs |
| | 2 | Rather more, still mid-line |
| | 3 & 4 | Half and full cover |
| 7. Lower abdomen | 1 | A few mid-line hairs |
| | 2 | A mid-line streak of hair |
| | 3 | A mid-line band of hair |
| | 4. | An inverted V-shaped growth |
| 8. Arm | 1 | Sparse growth affecting not more than a quarter of the limb surface |
| | 2 | More than this; cover still incomplete |
| | 3 & 4 | Complete cover, light and heavy |
| 9. Forearm | 1,2,3,4 | Complete cover of dorsal surface; 2 grades of light and 2 of heavy growth |
| 10. Thigh | 1,2,3,4 | As for arm |
| 11. Leg | 1,2,3,4 | As for arm |

TABLE 2

Grading of Acne, Seborrhea and Hair Loss

Acne

1. Isolated pustules, up to 10 in number
2. More than 10 isolated pustules
3. Clusters of pustules
4. Confluent pustules Seborrhea 1. Mild
2. Moderate
3. Severe Hair Loss 1. Mild
2. Obvious thinning
3. Very obvious thinning
4. Baldness Preferred compounds for use in the invention include synthetic progestins, anabolic steroids and other steroidal compounds having a Ki value of less than $2\times10^{-8}M$ for the androgen receptor, an androgen receptor-mediated inhibitory effect on the growth of human breast cancer ZR-75-1 cells reaching half-maximal value at a concentration below 3.0 nanomoles per liter, and lacking the masculinizing activity discussed above. Preferred androgens of the invention would cause no significant increase in the average masculinizing effect (e.g. a significant increase in any of the numerical grades set forth in Tables 1 or 2 above) observed in females following treatment for three months with blood concentrations of the androgen maintained at the top of the claimed concentration range (e.g. 50 nanomoles per liter). For most female patients for whom no masculinizing effects were visible prior to treatment, or a total score of 10 or less for all 11 sites indicated in Table 1 prior to treatment, the same score would normally be maintained during treatment in accordance with the present invention. That is, there would be no visible masculinizing effects after three months of treatment. For female patients displaying some masculinizing effects prior to treatment, it would be expected that those effects would not be increased by treatment.

To determine whether the Ki values are below $2\times10^{-8}M$, Ki values may be determined by the following method for measuring the affinity of various compounds for the androgen receptor.

Preparation of prostatic tissue

Ventral prostates are from Sprague-Dawley rats (Crl:CD (SD)Br) (obtained from Charles River, St-Constant, Québec) weighing 200–250 g and castrated 24 h before sacrifice. Immediately after removal, prostates are kept on ice and used for the androgen binding assays.

Preparation of cytosol

Prostatic tissues are finely minced with scissors (fresh tissue) or pulverized with a Thermovac system (frozen tissue) before homogenization in buffer A (Tris, 0.025M; monothioglycerol, 20 mM; glycerol, 10% (v/v); EDTA, 1.5 mM and sodium molybdate, 10 mM, pH 7.4) in a 1:5 ratio (w/v) using a Polytron PT-10 homogenizer. These and all the following procedures are performed at 0°–4° C. The homogenate is centrifuged at 105000×g for 1 h in order to obtain the cytosolic fraction in the supernatant.

Cytosolic androgen receptor assay

Aliquots of 100 μl are incubated at 0°–4° C. for 18 h with 100 μl of 3 nM [$^3$H]T or [$^3$H] R1881 in the presence or absence of increasing concentrations of the non-labeled androgenic compound to be tested. At the end of the incubation, free and bound T or R1881 are separated by the addition of 200 μl dextran-coated charcoal (1% charcoal, 0.1% dextran T-70, 0.1% gelatin, 1.5 mM EDTA and 50 mM Tris (pH 7.4)) for 15 min before centrifugation at 2300×g for another 15 min at 0°–4° C. Aliquots (350 μl) of the supernatant are transferred to scintillation vials with 10 ml of an aqueous counting solution (Formula 963, New England Nuclear) before counting in a Beckman LS 330 counter (30% efficiency for tritium).

Ki calculation

Apparent inhibition constant "Ki" values are calculated according to the equation $Ki=IC_{50}/(1+S/K)$ (Cheng and Prusoff, Biochem. Pharmacol. 22: 3099–3108, 1973). In this equation, S represents the concentration of [$^3$H]T or [$^3$H] R1881, K is the dissociation constant ($K_D$) of T or R1881 and $IC_{50}$ is the concentration of unlabeled compounds giving a 50% inhibition of T or R1881 binding. For numerous compounds, Ki values are reported in the literature. See, for example, Ojasso et al., J. Ster. Biochem. 27: 255–269, 1987; Asselin et al., Cancer Res. 40: 1612–1622, 1980; Toth and Zakar J. Steroid Biochem. 17: 653–660, 1982. A method giving similar results is described in Poulin et al., Breast Cancer Res. Treatm. 12: 213–225, 1988.

In order to determine the concentration at which a given compound reaches half-maximal androgen receptor-mediated inhibitory effect on the growth of human breast cancer ZR-75-1 cells, the following technique is utilized as described in detail in Poulin et al., Breast Cancer Res. Treatm. 12: 213–225, 1988.

Maintenance of stock cultures

The ZR-75-1 human breast cancer cell line can be obtained from the American Type Culture Collection (Rockville, Md.). The cells are routinely cultured in phenol red-free RPMI 1640 medium supplemented with 10 nM $E_2$, 15 mM Hepes, 2 mM L-glutamine, 1 mM sodium pyruvate, 100 IU penicillin per ml, 100 μg streptomycin sulfate per ml, and 10% (v/v) fetal bovine serum (FBS), in a water-saturated atmosphere of 95% air: 5% $CO_2$ at 37° C.

Stock cultures in their logarithmic growth phase are harvested with 0.05% trypsin/0.02% EDTA (w/v) in Hanks' balanced salts solution and resuspended in $E_2$- and phenol red-free RPMI 1640 medium containing 5% (v/v) dextran-coated charcoal (DCC)-treated FBS and 500 ng of bovine insulin per ml, but otherwise supplemented as described above for maintenance of stock cultures. Cells were plated in 24well Linbro culture plates (Flow Laboratories) at a final density of 0.5–4.0×$10^4$ cells/well.

Fourty-eight hours after plating, fresh SD medium containing the appropriate concentrations of steroids are added. The final concentration of ethanol used for the addition of test substances does not exceed 0.12% (v/v) and has no significant effect on cell growth and morphology. The incubation media are replaced every other day and cells are harvested by trypsinization after 12 days of treatment, unless otherwise indicated. Cell number can be determined with a Coulter Counter.

Calculations and statistical analyses

Apparent $IC_{50}$ values are calculated using an iterative least squares regression (Rodbard, Endocrinology 94: 1427–1437, 1974), while apparent inhibition constants (Ki values) are calculated according to Cheng and Prusoff (Biochem. Pharmacol. 22: 3099–3108, 1973).

DETAILED DESCRIPTION OF THE PREFERRED EMBODIMENTS

A better understanding of the multiple endocrine activity of synthetic progestins is required not only for their more rational use in the prevention and therapy of breast and endometrial cancers as well as endometriosis and bone loss but also to avoid side effects caused by interaction with steroid receptors unnecessary for the desired beneficial effect.

Precise analysis of the biological actions of synthetic "progestins" having affinity for many steroidal receptors would ideally require the selection of in vitro models possessing functional receptors for all major classes of steroids. For this purpose, we have chosen the ZR-75-1 human breast cancer cell line, which possesses functional receptors for estrogens, androgens, progesterone and glucocorticoids (Vignon et al., J. Clin. Endocrinol. Metab. 56: 1124–1130, 1983) in order to compare the relative contribution of the different steroid receptor systems in the control of cell proliferation by synthetic progestins. While estrogens are strongly mitogenic in ZR-75-1 cells (Poulin and Labrie, Cancer Res. 46: 4933–4937, 1986) and specifically regulate the expression and/or the secretion of several proteins (Dickson and Lippman, Endocr. Rev. 8: 29–43, 1987), androgens (Poulin et al., Breast Cancer Res. Treatm. 12: 213–225, 1988), glucocorticoids (Hatton, A. C., Labrie, F., unpublished results) as well as progestins (Poulin et al., Breast Cancer Res. Treatm. 13: 161–172, 1989) inhibit their proliferation through specific interactions with their respective receptors.

Many progestins have been used in the treatment of breast cancer, including MPA (Blossey et al., Cancer 54: 1208–1215, 1984; Hortobayyi et al., Breast Cancer Res. Treatm. 5: 321–326, 1985), MGA (Johnson et al., Semin. Oncol. 13 (Suppl.): 15–19, 1986; Tchekmedyan et al., Semin. Oncol. 13 (Suppl.): 20–25, 1986) and norethindrone (Clavel et al., Eur. J. Cancer Clin. Oncol. 18: 821–826, 1982; Earl et al., Clin. Oncol. 10: 103–109, 1984). Using the in vitro system of human breast cancer ZR-75-1 cells, I have found that the synthetic progestins or anabolic steroids, Nor-testosterone, R1881, dromostanolone, fluoxymesterone, ethisterone, methandrostanolone, oxandrolone, danazol, stanozolol, calusterone, oxymetholone, cyproterone acetate, chlormadinone acetate and norgestrel, possess androgenic activity at low concentrations. In addition to inhibition of cell growth, the secretion of two glycoproteins, namely gross cystic disease fluid protein-15 (GCDFP-15) and GCDFP-24 is markedly stimulated by androgens (Simard et al., Mol. Endocrinol. 3: 694–702, 1989; Simard et al., Endocrinology 126: 3223–3231, 1990). Measurements of GCDFP-25 or GCDFP-24 secretion can thus be used as sensitive parameter or marker of androgen action in these cells. In fact, changes in GCDFP-15 and GCDFP-24 secretion are opposite to the changes in cell growth under all experimental conditions examined. All the synthetic progestins or anabolic steroids that I have studied exhibit androgenic activity on ZR-75-1 breast cancer growth and secretion of GCDFP-15 and GCDFP-24.

Identification of the receptors (estrogen, androgen, progesterone and glucocorticoid) responsible for the action of the compounds is essential in order to assess the potential actions (including adverse effects) of such compounds. It is thus especially important to assess the specific interaction at low concentrations with the androgen receptor since such low concentrations do not interact with the glucocorticoid receptor, thus avoiding or minimizing secondary side effects.

One method for inhibiting growth of breast and endometrial cells is activation of the androgen receptor with an effective compound having an affinity for the receptor site such that is binds to the androgen receptor at low concentrations while not significantly activating other classes of steroid receptors linked to potential side effects. It is important to select compounds having maximal affinity for the androgen receptor which have minimal or no virilizing effects in women. In order to minimize interaction of such compounds with the glucocorticoid and estrogen receptors, it is important to use low dose of the compounds. It is also important to choose steroids having androgenic activity at low concentrations which are not metabolized into estrogens under in vivo conditions which, at the low concentrations used, will not lead to significant activation of receptors other than the androgen receptors.

My research has shown that the compounds used in the invention, particularly anabolic steroids and synthetic progestins, vary markedly, over different concentrations, in their ability to activate different classes of steroidal receptors. Hence, by carefully controlling concentration, it is possible to selectively cause activation of desired receptors while not causing significant activation of undesired receptors. For example, at the low concentrations specified herein, MPA can be utilized to desirably activate androgen receptors while substantially avoiding side effects associated with glucocorticoid activation which have plagued prior art treatments.

Thus, this invention provides a novel method for prevention and therapy of breast and endometrial cancer as well as other diseases responsive to activation of the androgen receptor, e.g. bone loss and endometriosis. In this invention, the amount of the androgenic compounds administered is much lower than previously used in art for the treatment of breast and endometrial cancer.

MONITORING BLOOD CONCENTRATION OF ANDROGENS OF THE INVENTION

To help in determining the potential effects of the treatment, blood concentrations of the compound can be measured. For example, measurements of plasma medroxyprogesterone acetate (MPA) levels can be made by radioimmunoassay following extraction as follows:

Antibody preparation

Antibody 144A was raised in rabbits against 17-hydroxyprogesterone-3-O-carboxymethyloxime-BSA. The labeled steroid used in the radioimmunoassay (RIA) was methyl-17α-hydroxyprogesterone acetate, 6α-[1,2-$^3$H (N)]- obtained from NEN (CAT NO: NET 480) while the reference preparation was medroxyprogesterone acetate (MPA) obtained from Steraloids. The assay buffer used was 0.1% gelatin in 0.1M sodium phosphate, 0.15M sodium chloride, 0.1% sodium azide, pH 7.2. The extraction solvent mixture was ethyl etheracetone (9:1, v:v) [EEA] while the LH-20 chromatography solvent mixture was iso-octane: toluene: methanol (90:5:5;v:v:v) [IOTH].

Extraction procedure

One ml of plasma was extracted twice with 5 ml of EEA. The extracts were evaporated to dryness with nitrogen and the remaining residue was dissolved in one ml of IOTH. The extracts were then subjected to LH-20 chromatography on 10×30 cm columns (Corning CAT NO: 05 722A) filled with 2 g of LH-20 (Pharmacia). The gel was washed with 30 ml of IOTH before addition of one ml of sample and elution with IOTH. The first 6 ml were discarded. The following 10, 16.5 and 27.5 ml of eluent were fraction I (progesterone), II (MPA) and III (17-LH-progesterone), respectively. Fraction II was evaporated to dryness and reconstituted in 1.5 ml of assay buffer.

Radioimmunoassay

To each 12'75 mm borosilicate test tube was added: 0.2 ml containing 25,000 DPM of tritiated steroid, 0.5 ml of reference preparation ranging from 5 to 5000 pg/tube or 0.5 ml of extracted sample fraction II, 0.2 ml of antiserum 144A diluted 1/5000 or 0.2 ml of assay buffer to account for non specific binding. The tubes were then incubated overnight at 4° C. Then, 0.2 ml 2% charcoal Norit-A, 0.2% Dextran T-70 diluted in water was added. The tubes were then shaken gently and, after 10 min, they were centrifuged at 2000×g for 10 min. The supernatant was mixed with 8 ml of Formula-989 (NEN: NEF-989) and the radioactivity was counted in a β-counter.

The lower and upper limits of detection of MPA are 10 and 10000 pg/ml, respectively, while the slope (LOGIT-LOG) is −2.2 and the $ED_{50}$ value is 315 pg/ml. Non-specific and net binding are 1.5 and 45%, respectively. Antibody 144A is highly specific for MPA since cross-reactivity with progesterone, 20α-OH-Prog, pregnenolone, 17-OH-pregnenolone, DHT, androstenedione, testosterone, 3α-diol, estrone, estradiol and cortisol is less than 0.1%.

Calculations and statistics

RIA data were analyzed using a program based on model II of Roadbard and Lewald (In: 2nd Karolinska Symposium, Geneva, 1970, pp. 79–103). Plasma MPA levels are usually shown as the means±SEM (standard error of the mean) of duplicate measurements of individual samples. Statistical significance is measured according to the multiple-range test of Duncan-Kramer (Kramer, C. Y., Biometrics 12: 307–310, 1956).

A test compound's relative effect on various receptors

To assist in determining the activity of the potential compounds on the various steroid receptors, androgen, glucocorticoid, progesterone and estrogen-receptor-mediated activities of synthetic progestins and anabolic steroids can be measured in ZR-75-1 human breast cancer cells using cell growth as well as GCDFP-15 and GCDFP-24 release as parameters of response (Poulin and Labrie, Cancer Res. 46: 4933–4937, 1986; Poulin et al., Breast Cancer Res. Treatm. 12: 213–225, 1988; Poulin et al., Breast Cancer Res. Treatm. 13: 161–172, 1989; Poulin et al., Breast Cancer Res. Treatm. 13: 265–276, 1989; Simard et al., Mol. Endocrinol. 3: 694–702, 1989; Simard et al., Endocrinology 126: 3223–3231, 1990).

The following properties permit measurement of progesterone receptor (PgR) activity: 1) the addition of insulin completely reverses the inhibition due to the interaction of the progestin RS020 with the PgR in ZR-75-1 cells; and 2) the antiproliferative effect of R5020 is observed only under $E_1$-stimulated conditions. These two characteristics of ZR-75-1 cell growth permit study of the extent to which a tested compound's effects on ZR-75-1 cells are attributated to its interaction with PgR by evaluating the effect of insulin and/or estrogen addition on the growth response measured at the end of a 15-day incubation of ZR-75-1 cells with the test compounds.

The contribution of the estrogen receptor (ER), on the other hand, can be directly measured by incubating ZR-75-1 cells in the presence or absence of estrogen in the medium.

In order to analyze the interactions of synthetic progestins or anabolic steroids with the androgen receptor (AR) and glucocorticoid receptor (GR) in their inhibitory action on cell growth, one takes advantage of the additivity of the anti-proliferative effects of androgens and glucocorticoids in this cell line (Poulin et al., Breast Cancer Res. Treatm. 12: 213–225, 1988; Hatton and Labrie, F., unpublished data). Thus, one can saturate AR with 5α-dihydrotestosterone (DHT) and then measure the effect on cell proliferation resulting from the addition of a putative glucocorticoid. On the other hand, the effect of a putative androgen can similarly be measured following saturation of GR by dexamethasone (DEX). The specificity of the growth-inhibitory activity thus observed with the test compound can also be further assessed by its reversibility using the appropriate antagonist (i.e. antiglucocorticoid or antiandrogen). Thus, in the presence of excess androgen (1 µM DHT) in the presence of $E_2$ and insulin, glucocorticoid effects can be assessed with precision and with no interference by the other receptors. The same applies to study of the role of AR when the cells are incubated in the presence of excess glucocorticoid (3 µM DEX), in the presence of $E_2$ and insulin. As demonstrated by detailed kinetic studies, 1 µM DHT and 3 µM DEX exert maximal inhibitory effects on the AR and GR, respectively.

In addition, the possible antagonistic activities of "progestins" mediated through the AR and GR can be determined by saturating both receptor systems with DHT and DEX with one ligand being in far greater excess than the other in order to allow reversal through a single chosen receptor at a time. All experiments are performed with ZR-75-1 cells grown in $E_2$-supplemented media containing insulin in order to prevent the PgR-mediated effect of "progestins" on cell growth.

Using the foregoing techniques, I have found that numerous androgenic compounds which also activate other receptors (e.g. glucocorticoid or progesterone receptors) vary in their relative effects on different receptors as a function of concentration. By staying within concentration ranges defined herein, compounds of the invention may beneficially affect androgen receptors without substantial undesirable effects on other receptors.

Selection of patients who may benefit from the method's described herein

The appearance of breast cancer is usually detected by self breast examination and/or mammography. Endometrial cancer, on the other hand, is usually diagnosed by endometrial biopsy. Both cancers can be diagnosed and evaluated by standard physical methods well known to those skilled in the art, e.g. bone scan, chest X-Ray, skeletal survey, ultrasonography of the liver and liver scan (if needed), CAT scan, MRI and physical examination. Endometriosis can be diagnosed following pains or symptoms associated with menstruations in women while definitive diagnosis can be obtained by laparoscopy and, sometimes, biopsy.

Bone density, on the other hand, can be measured by standard methods well known to those skilled in the art, e.g. QDR (Quantitative Digital Radiography), dual photon absorptiometry and computerized tomography. Plasma and urinary calcium and phosphate levels, plasma alkaline phosphatase, calcitonin and parathormone concentrations, as well as urinary hydroxyproline and calcium/creatinine ratios.

Breast or endometrial cancer, osteoporosis or otherwise insufficient bone mass, and other diseases treatable by activating androgen receptor may be treated in accordance with the present invention or prophylactically prevented in accordance herewith.

Typically suitable androgenic compounds include 6-alpha-methyl,17-alpha-acetoxy progesterone or medroxyprogesterone acetate available, for example, from Upjohn and Farmitalia Carlo Erba, S.p.A. under the trade names Provera, DepoProvera or Farlutal, and the acronym MPA.

Other suitable androgenic compounds include those described in Labrie et al. (Fertil. Steril. 31: 29–34, 1979) as well as anabolic steroids or progestins (Raynaud and Ojasso, In: Innovative Approaches in Drug Research, Elsevier Sci. Publishers, Amsterdam, pp. 47–72, 1986; Sandberg and Kiraoni, Pharmac. Ther. 36: 263–307, 1988; and Vincens, Simard and De Lignières, Les Androgènes. In: Pharmacologie Clinique, Base de Thérapeutique, 2ième Edition, Expansion Scientifique (Paris), pp. 2139–2158, 1988), as well as Calusterone (7β,17α-dimethyltestosterone), anabolic steroids (Lam, Am. J. Sports Medicine 12, 31–38, 1984; Hilf, R., Anabolic-androgenic steroids and experimental tumors. In: (Kochachian, C. D., eds.), Handbook of Experimental Pharmacology, vol. 43, Anabolic-Androgenic Steroids, Springer-Verlag, Berlin, 725 pp, 1976), fluoxymesterone (9α-fluoro-11β-hydroxy-17α-methyltestosterone), testosterone 17β-cypionate, 17α-methyltestosterone, Pantestone (testosterone undecanoate), $\Delta^1$-testololactone and Andractim.

Other typical suitable androgenic compounds are cyproterone acetate (Androcur) available from Shering AG, 6-alpha-methyl, 17-alpha-acetoxy progesterone or medroxyprogesterone acetate (MPA) available from, among others, Upjohn and Farmitalia, Calbo ERba, Gestodene available from Shering, megestrol acetate (17α-acetoxy-6-methyl-pregna-4,6-diene-3,20-dione) available from Mead Johnson & Co., Evanswille, Ind., under the trade name of Megace. Other synthetic progestins include Levonorgestrel, Norgestimate, desogestrel, 3-ketodesogestrel, norethindrone, norethisterone, 13α-ethyl-17-hydroxy-18, 19-dinor-17β-pregna-4,9,11-triene-20-yn-3one (R2323, gestrinone), demegestone, norgestrienone, gastrinone and others described in Raynaud and Ojasso, J. Steroid Biochem. 25: 811–833, 1986; Raynaud et al., J. Steroid Biochem. 25: 811–833, 1986; Raynaud et al., J. Steroid Biochem. 12: 143–157, 1980; Raynaud, Ojasoo and Labrie, Steroid Hormones, Agonists and Antagonists, In: Mechanisms of Steroid Action (G. P. Lewis and M. Ginsburg, eds), McMillan Press, London pp. 145–158 (1981). Any other progestin derivative having the above-described characteristics could also be useful for the invention.

The androgenic compound is preferably administered as a pharmaceutical composition via topical, parenteral or oral means. The compound can be administered parenterally, i.e. intramuscularly or subcutaneously by injection of infusion by nasal drops, by suppository, or where applicable intravaginally or transdermally using a gel, a patch or other suitable means. The androgenic compound may also be microencapsulated in or attached to a biocompatible, biodegradable polymer, e.g. poly(d1,1-lactide-co-glycolide) and subcutaneously or intramuscularly injected by a technique called subcutaneous or intramuscular depot to provide continuous, slow release of the compound over a period of 30 days or longer. In addition to the oral route, a preferred route of administration of the compound is subcutaneous depot injection. DepoProvera can be released at a relatively constant rate for approximately 3 months after intramuscular administration of an aqueous suppression.

The amount of each compound administered is determined by the attending clinician taking into consideration the patient's condition and age, the potency of each component and other factors. In the prevention of breast and endometrial cancer, as well as bone loss, according to this invention, the following dosage ranges are suitable.

The androgenic composition is preferably administered in a daily dosage which delivers less than 25 mg of active androgenic steroid per 50 kg of body weight.

A dosage of 1–10 mg per 50 kg of body weight, especially 3–7 mg (e.g. 5 mg) is preferred. The dosage selected preferably maintains serum concentration below 50 nanomoles per liter, preferably between 1.0 nanomoles per liter and 10, 15 or 25 nanomoles per liter depending on patient's response. The dosage needed to maintain these levels may vary from patient to patient. It is advisable for the attending clinical to monitor levels by the techniques described herein and optimize dosage accordingly. For prophylactic purposes, administration of the androgen is preferably started in the perimenopausal period for the prevention of breast and endometrial cancer and bone loss in normal women. The androgen may be associated with an accepted dose of an estrogen used to prevent other signs and symptoms of menopause. In women, when estrogen formation and/or action has been blocked for treatment of endometriosis, leiomyomata, breast cancer, uterine cancer, ovarian cancer or other estrogen-sensitive disease, administration of the androgen can be started at any time, preferably at the same time as blockade of estrogens.

The androgen for intramuscular or subcutaneous depot injection may be microencapsulated in a biocompatible, biodegradable polymer, e.g., poly(d,1-lactide-co-glycolide) by, among other techniques, a phase separation process or formed into a pellet or rod. The microspheres may then be suspended in a carrier to provide an injectable preparation or the depot may be injected in the form of a pellet or rod. See also European patent application EPA No. 58,481 published Aug. 25, 1982 for solid compositions for subdermal injection or implantation or liquid formulations for intramuscular or subcutaneous injections containing biocompatible, biodegradable polymers such as lactide-glycolide copolymer and active compounds. These formulations permit controlled release of the compound.

The androgens useful in the present invention can be typically formulated with conventional pharmaceutical excipients, e.g., spray dried lactose and magnesium stearate into tablets or capsules for oral administration.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g., of hard gelatin, as well as closed soft-gelatin capsules comprising a softener or plasticizer, e.g. glycerine. The plus capsules contain the active substance preferably in the form of granulate, e.g., in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

In place of oral administration, the active compound may be administered parenterally. In such case, one can use a solution of the active substance, e.g., in sesame oil or olive oil. The active substance can be microencapsulated in or attached to a biocompatible, biodegradable polymer, e.g. poly(d,1-lactide-co-glycolide) and subcutaneously or intramuscularly injected by a technique called subcutaneous or intramuscular depot to provide continuous slow release of the compound(s) for a period of 2 weeks or longer.

The invention also includes kits or single packages containing the pharmaceutical composition active ingredients or means for administering the same for use in the prevention and treatment of breast and endometrial cancer as well as bone loss and treatment of endometriosis as discussed above. The kits or packages may also contain instructions on how to use the pharmaceutical compositions in accordance with the present invention.

Following the above therapy using the described regimen, tumor growth of breast and endometrial cancer as well as bone loss and endometriosis can be relieved while minimizing adverse side effects. The use of the described regimen can also prevent appearance of the same diseases.

EXAMPLE 1

Prevention of Mammary Carcinoma Induced by Dimethylbenz(a)anthracene (DMBA) in the Rat, By Low Dose Medroxyprogesterone Acetete ("MPA").

Figure 1:
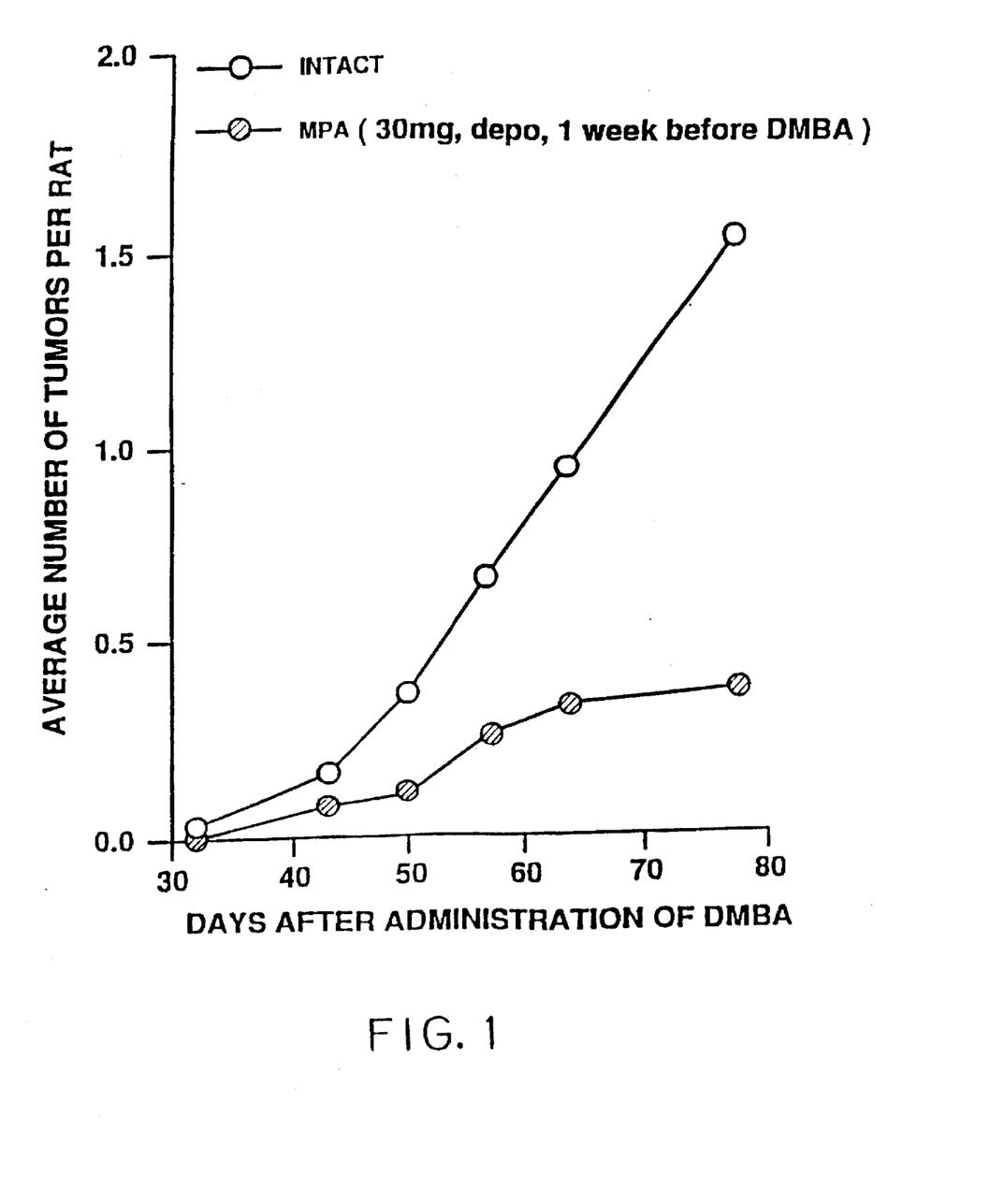
FIG. 1 is a comparative graph over time of the number of tumors observed in a group of rats protected by a method in accordance with the invention following administration of dimethylbenz(a)anthracene (DMBA) versus an unprotected control group.

To illustrate the efficacy of the present invention in reducing the incidence of mammary carcinoma, FIG. 1 illustrates the effect of a single subcutaneous injection of Depo-Provera (Medroxyprogesterone Acetate (MPA) (30 mg)) one week before inducing carcinoma with dimethylbenz(a)anthracene. FIG. 1 shows the period from 30 to 85 days following administration of DMBA. One curve in FIG. 1 shows the average number of tumors per animal in the group protected by Depo-Provera while the other curve shows the average number of tumors per animal in the unprotected group. It is estimated that the 30 mg. injection of Depo-Provera would release approximately 0.17 mg. of active medroxyprogesterone acetate per day over a six-month period. As may be seen by comparing the two graphs in FIG. 1, the Depo-Provera-treated group showed much greater resistance to the development of tumors than did the unprotected group. After 85 days an average of 1.89 tumors per rat was observed in the unprotected group, while only 0.30 tumor per rat was observed in the Depo-Provera protected group. Tumor number and size measured with calipers were determined weekly.

EXAMPLE 2

Figure 2:
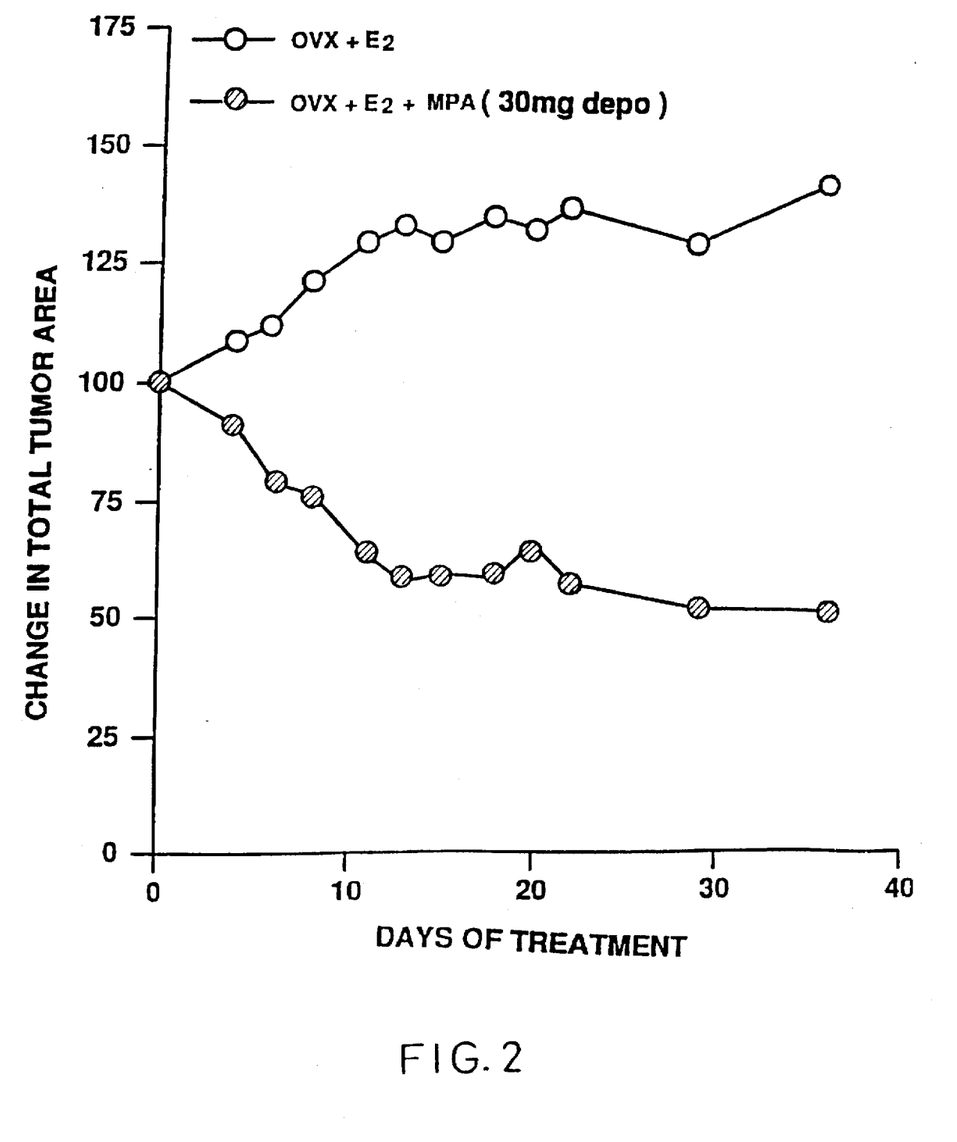
FIG. 2 is a comparative graph of estradiol-stimulated growth of tumors in ovariectomized rats treated in accordance with the invention versus an untreated control group.

Treatment of Mammary Carcinoma Induced By Dimethylbenz(a)anthracene In the Rat, By Low Dose Medroxyprogesterone Acetate FIG. 2 illustrates the inhibition of mammary carcinoma growth which may be achieved in accordance with the methods of the invention. Tumors were induced in ovariectomized rats using dimethylbenz(a)anthracene. Estradiol was used to stimulate growth in both a treatment and control group of rats. Each animal in the treatment group received a single subcutaneous administration of 30 mg of Depo-Provera (which is estimated to release approximately 0.17 mg. per day of active medroxyprogesterone acetate for a period of about six months). This figure illustrates the average estradiol-stimulated change in total tumor area in each group following treatment. As may be seen in FIG. 2, the group treated with Depo-Provera exhibited significantly less tumor growth than the untreated group.

The terms and descriptions used herein are preferred embodiments set forth by way of illustration only, and are not intended as limitations on the many variations which those of skill in the art will recognize to be possible in practicing the present invention as defined by patent claims based thereon.

What is claimed is:

1. A method for treating endometriosis in a patient in need of such treatment, comprising administering to said patient at least one androgenic steroid having a Ki value for the androgen receptor of less than about $2 \times 10^{-8}$M and an androgen receptor-mediated inhibitory effect on the growth of human breast cancer ZR-75-1 cells which reaches half-maximal value at a concentration below 3.0 nanomoles per liter and no visible masculinizing activity wherein said androgenic steroid is administered at a dosage sufficiently low to maintain a cumulative androgenic steroid serum concentration below approximately 50 nanomoles per liter.

2. The method of claim 1, wherein said cumulative serum concentration is maintained between about 1 and 25 nanomoles per liter.

3. The method of claim 1, wherein said cumulative serum concentration is maintained between 1 and about 15 nanomoles per liter.

4. The method of claim 1, wherein said cumulative serum concentration is maintained between 1 and 10 nanomoles per liter.

5. The method of claim 1, wherein said androgenic steroid(s) is(are) administered together with a pharmaceutically acceptable diluent or carrier in a dosage which delivers less than 25 milligrams of such androgenic steroid(s) per 50 kilograms of body weight per day.

6. The method of claim 5, wherein said androgenic steroid(s) is(are) administered in an amount between about 1 and about 10 milligrams of said androgenic steroid(s) per 50 kilograms of body weight per day.

7. The method of claim 5, wherein said androgenic steroid(s) is(are) administered in an amount between about 3 and about 7 milligrams of said androgenic steroid(s) per 50 kilograms of body weight per day.

8. The method of claim 1, wherein at least one androgenic steroid is a synthetic progestin.

9. The method of claim 1, wherein at least one androgenic steroid is an anabolic steroid.

10. The method of claim 1, wherein at least one androgenic steroid is medroxyprogesterone acetate (17α-acetoxy-6α-methyl progesterone).

11. The method of claim 7, wherein at least one androgenic steroid is medroxyprogesterone acetate (17α-acetoxy-6α-methyl progesterone).

12. A method for treating endometriosis in a patient in need of such treatment comprising administering to said patient medroxyprogesterone acetate at a dosage sufficiently low to maintain serum concentration of said medroxyprogesterone acetate at less than about 50 nanomoles per liter.

13. The method of claim 12, wherein said dosage is between 1 and 10 milligrams per 50 kilograms of body weight per day.

14. A method for treating endometriosis in a patient in need of such treatment comprising administering to said patient megestrol acetate at a dosage sufficiently low to maintain serum concentration of said megestrol acetate at less than about 50 nanomoles per liter.

15. The method of claim 14, wherein said dosage is between 1 and 10 milligrams per 50 kilograms of body weight per day.

16. The method as recited in claim 1 wherein said patient is a human.

17. The method as recited in claim 12 wherein said patient is a human.

18. The method as recited in claim 14 wherein said patient is a human.

* * * * *